United States Patent [19]

Holmes

[11] Patent Number: 4,620,999

[45] Date of Patent: Nov. 4, 1986

[54] DISPOSABLE BAGS

[75] Inventor: Paul A. Holmes, North Yorkshire, England

[73] Assignee: Imperial Chemical Industries PLC, London, England

[21] Appl. No.: 668,201

[22] Filed: Nov. 5, 1984

[30] Foreign Application Priority Data

Nov. 15, 1983 [GB] United Kingdom ................ 8330414

[51] Int. Cl.$^4$ ........................ B65D 55/18; A61G 9/00
[52] U.S. Cl. ..................................... 428/35; 428/536; 428/543; 428/520; 428/913; 528/489; 528/499; 604/333
[58] Field of Search ................ 428/35, 536, 543, 913; 528/489, 499

[56] References Cited

U.S. PATENT DOCUMENTS

| | | | |
|---|---|---|---|
| 3,221,742 | 12/1965 | Orowan | 428/35 X |
| 3,400,717 | 9/1968 | Cubitt et al. | 128/284 |
| 3,546,716 | 12/1970 | Laumann | 428/913 X |
| 3,804,092 | 4/1974 | Tunc | 428/913 X |
| 3,808,165 | 4/1974 | Duchane | 428/913 X |
| 4,372,311 | 2/1983 | Potts | 428/507 X |

FOREIGN PATENT DOCUMENTS

WO79/00008 1/1979 PCT Int'l Appl. ................ 128/284

*Primary Examiner*—P. C. Ives
*Attorney, Agent, or Firm*—Cushman, Darby & Cushman

[57] ABSTRACT

Degradation of body-waste bags to assist disposal thereof in sewage systems is facilitated by addition of a base to raise the pH of the human fecal waste bag contents to at least about 12. Inter alia, there is provided a package of at least one bag and sufficient base, preferably in prepacked quantities, to treat all the bags in the package.

10 Claims, No Drawings

DISPOSABLE BAGS

This invention relates to disposable bags and in particular to body-waste bags for receipt of faeces and/or urine, for example incontinence bags and bed pan liners.

Incontinence bags are often worn by the incontinent or those who have undergone certain surgical operations, e.g. colostomy, so that the wearer's mobility is not restricted by virtue of the incontinence and/or operation.

Disposal of the bags after use creates problems since they are liable to cause obstructions in sewage pipes and in sewage treatment plants.

It has been proposed in U.S. Pat. No. 4,372,311 to make disposable articles from a water soluble polymer coated with a degradable polymer. Among the degradable polymers listed therein is poly(3-hydroxybutyrate). That specification suggests that upon degradation of the degradable polymer, the water soluble polymer can dissolve and hence obstruction of sewage pipes and sewage treatment plants would be avoided.

While 3-hydroxybutyrate polymers are well suited to the manufacture of body-waste bags, whether alone or as a coating on a water soluble polymer, by virtue of their good water and vapor impermeability characteristics, their rate of degradation is often too slow to avoid the formation of the aforementioned obstructions.

We have found that the rate of degradation can be markedly increased by modification of the pH of the bag contents.

Accordingly the present invention provides a method of disposal of a body-waste bag comprising a 3-hydroxybutyrate polymer and containing human faeces and/or urine including the steps of modifying the pH of the contents of the bag to a pH of at least about 12, and thereafter introducing said bag and contents into a sewage system.

The pH is conveniently modified by addition of a base to the bag contents. The base is preferably added as a solid.

Suitable bases include sodium hydroxide and sodium carbonate. To avoid handling hazards, the base is preferably added to the bag contents in the form of a container e.g. a capsule or sachet containing the requisite amount of the base, said container being made from a water soluble material such as polyvinyl alcohol. Alternatively the base can be added in the form of a pellet or powder having a coating of a suitable water soluble material, e.g. a water soluble polymer or sugar.

The amount of base that needs to be added to each bag will depend on the nature of the base, i.e. its strength, and on the volume, pH, and buffering capacity of the bag contents. Human faeces and urine generally have a pH in the range about 4.5 to about 8.5, but will not generally exert a significant buffering capability.

The useful, i.e. "working" capacity of the bag is generally no more than about 50% of the actual, i.e. total, capacity of the bag.

Generally it is desirable that the user adds a standard amount, preferably a prepacked amount, of the base to the bag contents irrespective of the degree of filling of the bag to be disposed or of the pH of the contents.

Accordingly the amount of base added is desirably sufficient to increase the pH of the contents of a bag half full of the body-waste at pH about 4.5 to at least about 12.

Where the base is sodium hydroxide or carbonate, the amount of base required is thus at least about 0.2 g of sodium hydroxide or at least about 5 g of sodium carbonate monohydrate per 100 ml of bag total capacity. Preferably the amount of base employed is 0.3 to 3 g of sodium hydroxide or 6 to 15 g of sodium carbonate monohydrate per 100 ml of bag total capacity.

The invention also provides a package including (i) at least one body-waste bag comprising a 3-hydroxybutyrate polymer, and (ii) sufficient of basic material to modify the pH of the contents of all of the bags in said packages, when said bags are half filled with human faeces and/or urine, to a value of at least about 12.

Consequently such a package should contain, where the base is sodium hydroxide or sodium carbonate, at least 0.2 xn, preferably 0.3 xn to 3 xn g of sodium hydroxide or 5 xn, preferably 6 xn to 15 xn g of sodium carbonate monohydrate, where n is the number of bags in the package and each bag has a total capacity of 100×ml.

Each bag preferably has a total capacity within the range 50 to 500 ml.

Accordingly the invention further provides a package including at least one body waste bag comprising a 3-hydroxybutyrate polymer and a base selected from sodium hydroxide and sodium carbonate monohydrate, the quantity of base in the package being at least 0.2 xn g of sodium hydroxide or at least 5 xn g of sodium carbonate monohydrate, where n is the number of said body waste bags in the package and each body waste bag has a total capacity of 100 ×ml.

In order to improve wetting of the 3-hydroxybutyrate polymer by the bag contents, in some cases the addition of a surfactant may be desirable. Such a surfactant may be incorporated in the package either as a separate ingredient or in admixture with the basic material.

The bag is conveniently constructed from a film: the film may be a laminate of a water soluble polymer film, such as a polyvinyl alcohol or polyethylene oxide film, and a 3-hydroxybutyrate polymer film or coating with the latter on the interior side of the bag. Preferably, where a laminar structure is employed, the laminate also has a film or coating of the 3-hydroxybutyrate polymer on the external surface of the bag so that the water soluble polymer is sandwiched between the 3-hydroxybutyrate polymer layers. In such a laminar or sandwich construction the, or each, 3-hydroxybutyrate polymer layer preferably has a thickness of 5 to 25 $\mu$m and the water soluble polymer film preferably has a thickness of 25 to 75 $\mu$m.

Alternatively the film used to make the bag may be of non-laminar construction and may be a 3-hydroxybutyrate film or sheet, preferably of thickness 25 to 100 $\mu$m.

3-Hydroxybutyrate polymers may be made microbiologically, for example by the techniques described in European Patent Publications 15669 and 46344. Microbiologically produced 3-hydroxybutyrate copolymers, for example as described in European Patent Publications 52459 and 69497 may be employed if desired: the use of copolymers, for example containing 10 to 25, particularly 15 to 20 mole % of 3-hydroxyvalerate units may in some cases be advantageous to lower the modulus of the 3-hydroxybutyrate polymer since then bags made from a film of such copolymers are less liable to make rustling noises upon movement of the wearer.

The 3-hydroxybutyrate polymer may be extracted from the micro-organism by the techniques disclosed in European Patent Publications 15123, 36699, 46017 and 46335. Films or coatings of the 3-hydroxybutyrate polymer may be made by solution coating techniques or by melt extrusion.

In some cases it may be desirable to fabricate the film or coating from a plasticised 3-hydroxybutyrate polymer: suitable plasticisers include aryl sulphonamides and triphenyl phosphate.

The use of an aryl sulphonamide, such as o,p-toluene sulphonamide, as a plasticiser, in addition to improving the physical characteristics of the film, has the further advantage that, upon addition of the base to the bag contents, the sulphonamide tends to give the corresponding aryl sulphonate which acts as a transesterification catalyst thereby enhancing the rate of breakdown of the 3-hydroxybutyrate polymer.

The invention is illustrated by the following Examples.

EXAMPLE 1

In this example the effect of acids and bases on the degradation rate of a film of a 3-hydroxybutyrate polymer is illustrated.

A film of thickness 40 μm was cast from a solution of a 3-hydroxybutyrate copolymer containing 17 mole % of 3-hydroxyvalerate units in methylene chloride. The solution also contained 20% by weight, based on the weight of the 3-hydroxybutyrate copolymer of o,p-tuluene sulphonamide as a plasticiser. The film was cut into strips 6 cm long and 1 cm wide. The film samples were immersed in the appropriate aqueous solution at room temperature and agitated gently. Samples were removed at intervals and the tensile properties assessed. The results were as follows:

|   | Solution | pH | Tensile properties of film |
|---|---|---|---|
| 1. | water | ~7 | negligible change after 6 hours immersion |
| 2. | 2N HCl | <1 | negligible change after 6 hours immersion |
| 3. | 3N NaOH | >14 | complete disintegration after about 20–30 minutes immersion |
| 4. | 2N NaOH | >14 | |
| 5. | N NaOH | ~14 | film rapidly lost strength and disintegrated after about 6 hours immersion |
| 6. | N/2 NaOH | >13 | film rapidly became brittle. Wetting of the film could be improved by addition of a surfactant. As the proportion of surfactant increased in the range 0.025 to 0.5% by weight of the solution, the rate of degradation of the film increased. |

EXAMPLE 2

A polyvinyl alcohol film of thickness 40 μm was coated on one side with the 3-hydroxybutyrate copolymer containing solution employed to make the cast film in Example 1, and the solvent allowed to evaporate to give a plasticised 3-hydroxybutyrate copolymer coating of 15 μm thickness.

The coated film was then fabricated into a colostomy bag of 100 ml total capacity with the 3-hydroxybutyrate copolymer coating on the inside.

To dispose of the bag after addition of about 50 ml of mixture of human urine and faeces, a pellet of 2 g of sodium hydroxide is added to the bag contents to raise the pH to above 14 and then the bag is sealed and placed in a W.C. pan.

Within a short period the bag distintegrates and largely dissolves enabling the pan to be flushed without risk of blockage of the sewage pipes.

EXAMPLE 3

A sachet was prepared from the plasticised copolymer film described in Example 1 by heat sealing two layers of film along three right angled edges. The resulting sachet was 15 cm long and 10 cm across the open end. The sachet was then half filled with approximately 50 ml of an aqueous medium designed to simulate the consistency of faecal wastes. This medium was prepared by adding 2.5 kg of sharp sand of particle size between 150 and 420 μm to 1 liter of an aqueous solution containing 20 g of high viscosity sodium carboxymethyl cellulose.

No leakage of the contents of the sachet occurred over a period of several days.

2 g of caustic soda prills were dropped into the half full sachet. The heat sealed edges began to leak after only a few minutes. The leaking sachet was then suspended over an empty beaker. The sachet failed catastrophically, releasing the contents within 5 minutes of addition of the caustic soda.

Similar results were obtained when the caustic soda was added in the form of prills sealed into a sachet fabricated from a water soluble polyvinyl alcohol (PVA) film since the PVA film disintegrated within a few seconds of being added to the sachet contents.

EXAMPLE 4

A solution containing 10% by weight of the copolymer employed in Example 1 and 2% by weight of o,p-toluene sulphonamide dissolved in chloroform was carefully spread on a polyvinyl alcohol film of thickness 40 μm and allowed to dry to give a plasticised copolymer coating of 15 μm thickness. The coated film was then turned over and a similar coat was applied to the other side of the polyvinyl alcohol film.

A sachet of this laminated film was prepared by heat sealing as described in Example 3 and 50 ml of the viscous faece waste simulating medium added. No leakage of the contents were observed over three days. However, when the 2 g of caustic soda were added, leakage occurred at the seal almost immediately and catastrophic failure of the seals occurred within 20 seconds causing release of the contents. The film remaining had the consistency of wet toilet paper and would not be expected to cause blockages in a domestic sanitation system.

I claim:

1. A package including at least one body-waste bag comprising a 3-hydroxybutyrate polymer and requisite amount of a basic material to modify the pH of the contents of all the body-waste bags in the package, at the time the bags are half filled with human faeces and/or urine, to a value of at least about 12.

2. A package according to claim 1 wherein the basic material is in a number of prepacked amounts at least equal to the number of bags in the package.

3. A package according to claim 2 wherein the basic material is prepacked in containers formed from a water-soluble polymer, each container containing the amount of base required to be added to one bag.

4. A package according to claim 1 wherein the basic material is selected from sodium hydroxide and sodium carbonate monohydrate.

5. A package according to claim 1 also containing a surfactant.

6. A package according to claim 1 wherein each bag is fabricated from a film of a water-soluble polymer coated or laminated, at least on one surface, with a layer of a 3-hydroxybutyrate polymer, each bag having a 3-hydroxybutyrate polymer layer at least on the interior surface of the bag.

7. A package according to claim 1 wherein the 3-hydroxybutyrate polymer is a 3-hydroxybutyrate/3-hydroxyvalerate copolymer.

8. A package according to claim 1 wherein the 3-hydroxybutyrate polymer contains an aryl sulphonamide plasticiser.

9. A package including at least one body-waste bag comprising a 3-hydroxybutyrate polymer and a basic material selected from sodium hydroxide and sodium carbonate monohydrate, the quantity of base in the package being at least 0.2 xn of sodium hydroxide or at least 5 xn g of sodium carbonate monohydrate, where n is the number of said body-waste bags in the package and each body-waste bag has a total capacity of 100 ×ml.

10. A method of disposal of a body-waste bag comprising a 3-hydroxybutyrate polymer and containing human faeces and/or urine including the steps of modifying the pH of the contents of the bag to a pH of at least about 12, and thereafter introducing said bag and contents into a sewage system.

* * * * *